Figure 1:
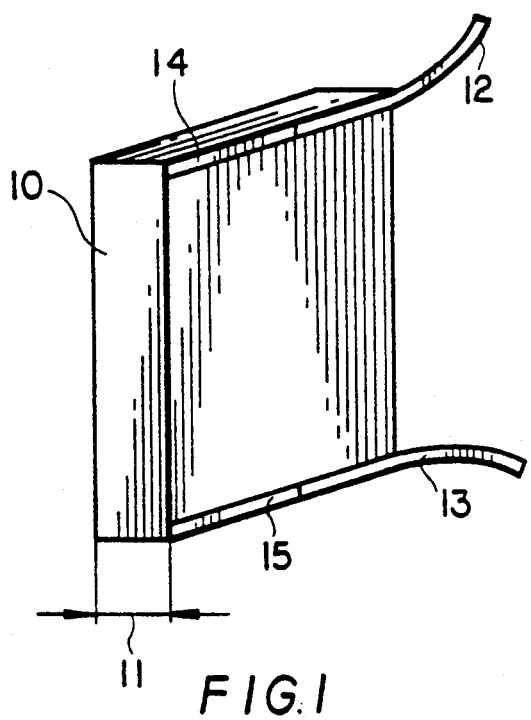

United States Patent [19]
Kanstad

[11] Patent Number: 5,220,173
[45] Date of Patent: Jun. 15, 1993

[54] PULSATING INFRARED RADIATION SOURCE

[75] Inventor: Svein O. Kanstad, Lødingen, Norway

[73] Assignee: Kanstad Teknologi a.s., Lodingen, Norway

[21] Appl. No.: 778,963

[22] PCT Filed: May 22, 1990

[86] PCT No.: PCT/NO90/00086
§ 371 Date: Nov. 21, 1991
§ 102(e) Date: Nov. 21, 1991

[87] PCT Pub. No.: WO90/14580
PCT Pub. Date: Nov. 29, 1990

[30] Foreign Application Priority Data
May 26, 1989 [NO] Norway ................................ 892117

[51] Int. Cl.$^5$ ............................................. G01J 1/00
[52] U.S. Cl. .............................. 250/493.1; 250/494.1; 250/495.1; 250/504 R; 250/505.1
[58] Field of Search ............... 250/493.1, 494.1, 495.1, 250/505.1, 504 R

[56] References Cited

U.S. PATENT DOCUMENTS

| | | | |
|---|---|---|---|
| 3,633,059 | 1/1972 | Nishizawa et al. | 357/20 |
| 4,620,104 | 10/1986 | Nordal et al. | 250/493.1 |
| 4,644,141 | 2/1987 | Hagen et al. | 250/493.1 |
| 4,859,080 | 8/1989 | Titus et al. | 250/494.1 |
| 4,859,859 | 8/1989 | Knodle et al. | 250/493.1 |
| 4,922,116 | 5/1990 | Grinberg | 250/495.1 |
| 5,128,514 | 7/1992 | Lehmann et al. | 250/493.1 |

Primary Examiner—Bruce C. Anderson
Attorney, Agent, or Firm—Ladas & Parry

[57] ABSTRACT

Pulsating infrared radiation source 50, which is so thin as to make its thermally stored energy less than the energy radiated during each pulse. This makes the source cooled by its own heat emission. Such sources have thicknesses commensurate with the wavelengths of infrared radiation. To avoid interference effects, the source's optical thickness may be made to equal a multiple of half wavelengths of the desired radiation. With the source mounted in a housing 53, efficient radiative cooling is obtained using windows 54 and 55 to each side. This makes it possible to extract infrared radiation from either face of the source.

25 Claims, 3 Drawing Sheets

PULSATING INFRARED RADIATION SOURCE

This invention relates to pulsating infrared radiation sources, particularly concerning their applications in infrared spectral analysis and in thermal printers. By designing the radiation source as given in this specification, one obtains larger temperature contrasts and smaller time constants than from similar sources presently known. This simplifies the making and improves the performance of equipment encompassing such sources.

All bodies and objects having a certain temperature emit thermal, electromagnetic radiation. For ideal black bodies, the emitted power per unit area within a wavelength interval $\delta\lambda$ at wavelength $\lambda$ is given by Planck's radiation law, $$W(\lambda, T)\delta\lambda = \frac{2\pi hc^2}{\lambda^5} (e^{\frac{hc}{kT\lambda}} - 1)^{-1} \delta\lambda, \quad (1)$$

in which T is the body's temperature, h is Planck's constant, k is Boltzmann's constant and c the velocity of light; $W(\lambda,T)$ is termed the spectral radiant excitance of the body. The spectral distribution of such thermal radiation has a pronounced maximum at a wavelength $\lambda_{max}$, which to good approximation is determined by the body's temperature through Wien's displacement law, $$T \cdot \lambda_{max} = 2897.9 \; [K \cdot \mu m]. \quad (2)$$

Thus with increasing temperature, the maximum point of the distribution becomes displaced towards shorter wavelengths according to (2). At either side of the maximum, the spectral distribution falls off strongly, very rapidly for decreasing $\lambda$ and more slowly for increasing $\lambda$'s.

Integration of (1) across all wavelengths $\lambda$ gives Stefan-Boltzmann's law for the total radiant excitance of the body, $$W = \sigma T^4, \quad (3)$$

where $\sigma = 5.67 \cdot 10^{-12}$ [W/cm$^2$K$^4$] is the Stefan-Boltzmann constant. For a 1000K radiator this corresponds to approximately 5 [W/cm$^2$]. Bodies not ideally black are most conveniently described by introducing a function $\epsilon < 1$ on the right hand side of eqs. (1) and (3); $\epsilon$ is termed the emissivity of the body. Materials whose $\epsilon$ is independent of $\lambda$ are called grey emitters.

When a body at temperature T is subjected to temperature variations of magnitude $\delta T$, corresponding variations are produced in the body's radiant excitance. At constant wavelength $\lambda$, $W(\lambda,T)$ always increases with rising temperature. Such spectral radiant contrast is largest in a range near $\lambda_{max}$. At the same time, the total radiant excitance W of a grey body varies by an amount $$\delta W = 4\epsilon \sigma T^3 \delta T. \quad (4)$$

In infrared spectroscopy as well as in thermal printers, large and rapid variations in radiative intensity from the thermal source are desireable. The classical infrared radiation sources, however, like Nernst and Globar radiators, operate at constant temperatures. That is also the case with more modern radiation sources, in which thin and electrically conducting films have been deposited onto thermally insulating substrates, cf. British patent 1.174.515, U.S. Pat. Nos. 3,694,624 and 3,875,413, and German Auslegeschrift 24.42.892. Variations in radiative intensity are then afforded by means of mechanically moveable shutters (choppers) interrupting the radiation. This results in large contrast in radiation between the hot source and the cold chopper blade. But it also constrains temperature variations to a fixed frequency, introduces complicating mechanically moveable parts, and obstructs electronic control of the radiation source contrary to other circuit components.

Norwegian patent 149.679 describes a pulsating infrared radiation source, comprising an electrically insulating substrate onto which has been deposited an electrically conducting film, where the thermal time constant of the source—given by the time required for thermal diffusion through the substrate—has been adjusted to suit the pulse frequencies at which the source is to operate. The source should then be made so thick as to thermally insulate, for the duration of the current pulse, the rear side of the substrate from the electrically conducting film on the front side. At the same time the source must be sufficiently thin to support heat diffusion through the substrate between pulses. This gives sources with typical substrate thicknesses of 0.1–1 mm.

However, radiation sources whose thicknesses are as given in the mentioned Norwegian patent, have thermal responses mainly determined by the substrate's thermal capacity. This may be illustrated by a 0.5 mm thick and 1 cm$^2$ wide substrate, made from a material with specific gravity 2 [g/cm$^3$] and specific thermal capacity 0.5 [J/g·K], which stores 0.5 J of thermal energy per 10K temperature difference. If the source is used to produce thermal radiation at 50 Hz, 25 W of electrical energy needs to be supplied. But at a temperature of 1000K, from (3) only 5 W of thermal power may be radiated, and only 0.2 W concurrent with the temperature variations according to (4). Energywise such a source thus is very inefficient. The majority of the electrically supplied energy becomes stored as heat in the substrate, to be continuously conducted away through the rear side and the ends, nearly 20% is lost as CW radiation, and less than 1% of the energy leaves the source as the desired radiation at 50 Hz. The source is also prone to mechanical fracture, since the periodic temperature differences between its front and rear sides subject the substrate to repeated bending strains.

U.S. Pat. No. 3,961,155 describes an element for thermal printers, whose main components are chiefly those of the source described above. The substrate's thickness is typically 0.5 mm, the element thus being subject to the same limitations as apply to sources according to Norwegian patent no. 149.679. None of the mentioned patent specifications solve the central problem about pulsating thermal radiation sources, which is to achieve large temperature contrasts at arbitrarily chosen pulse frequencies.

The present invention takes as its starting point that a large temperature contrast is, chiefly, a question of cooling the source between current pulses. This can be achieved by making the source radiation cooled, contrary to the sources discussed above which are cooled by heat conduction. Conduction of heat occurs by diffusion, which is a slow process, whereas thermal radiation is essentially instantaneous. The source must then be designed to make most of the electrically supplied energy radiate away thermally during the flow of the current pulse. A priori this results in a high thermal efficiency of the source, since the useful radiation is the same as that which cools the source. Ideally, then, very little thermal energy remains stored in the source after the current pulse, which energy is even further removed through continued thermal radiation. This happens in a time interval that may be short compared to the duration of the current pulse, resulting in a rapid and large drop in temperature after each current pulse.

In a radiation cooled source, the thermally stored energy is, in other words, less than and preferentially significantly less than the thermal energy radiated during each current pulse. Such sources are so thin that they become uniformly heated throughout their volume, thus they are also radiation cooled to both sides. From this one finds, by means of (4), that the thickness t of the source must satisfy the relation $$t < 8\epsilon\sigma T^3 / C\rho f, \qquad (5)$$

C being the specific thermal capacity of the source material, $\rho$ its density and f the pulse frequency of the desired radiation. For a material as in the example above, with $C = 0.5$ [J/g·K], $\rho = 2$ [g/cm$^3$] and $\epsilon = 1$, one finds $t < 4$ μm for $f = 100$ Hz. This is two orders of magnitude thinner than for sources as earlier described, which serves furthermore to emphasize the novelty of the basic conditions here laid down for the construction of efficient sources for pulsating infrared radiation.

Figure 2:
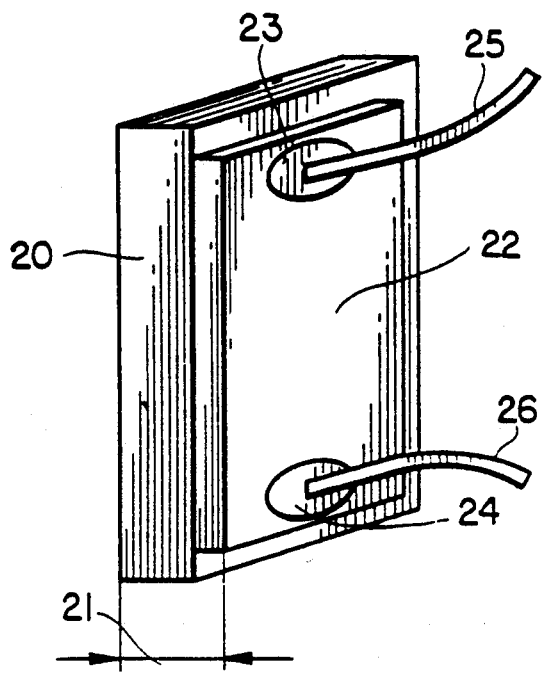
Figure 4:
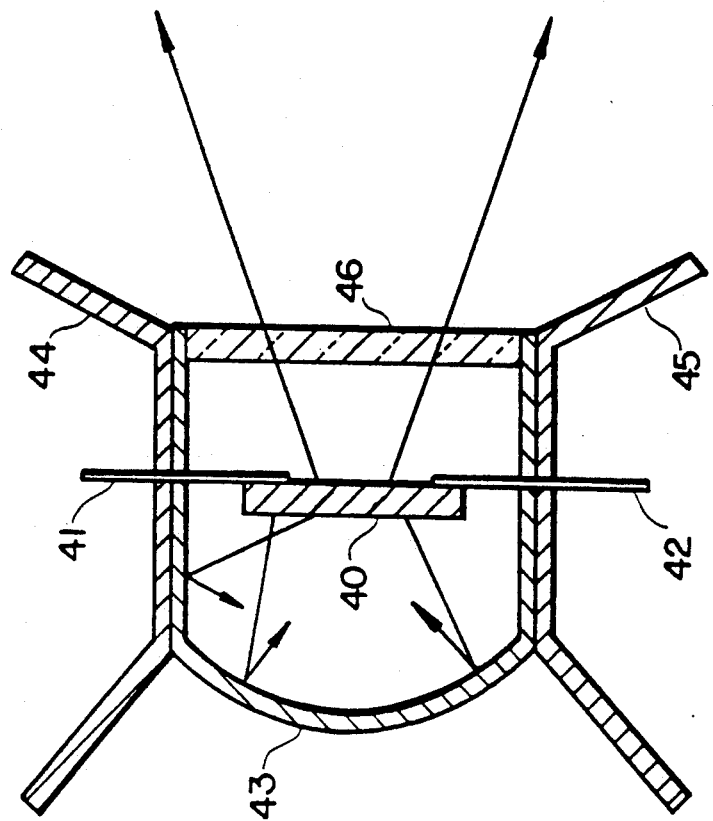
Figure 3:
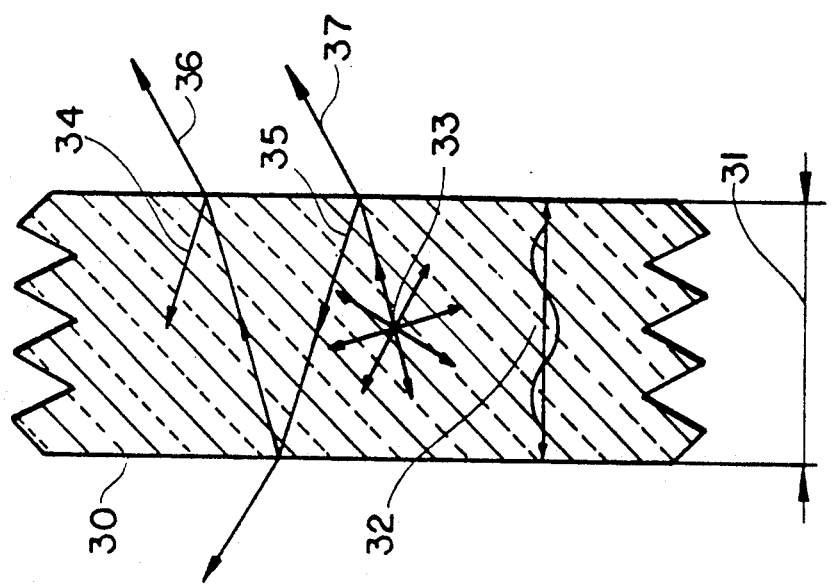
Figure 5:
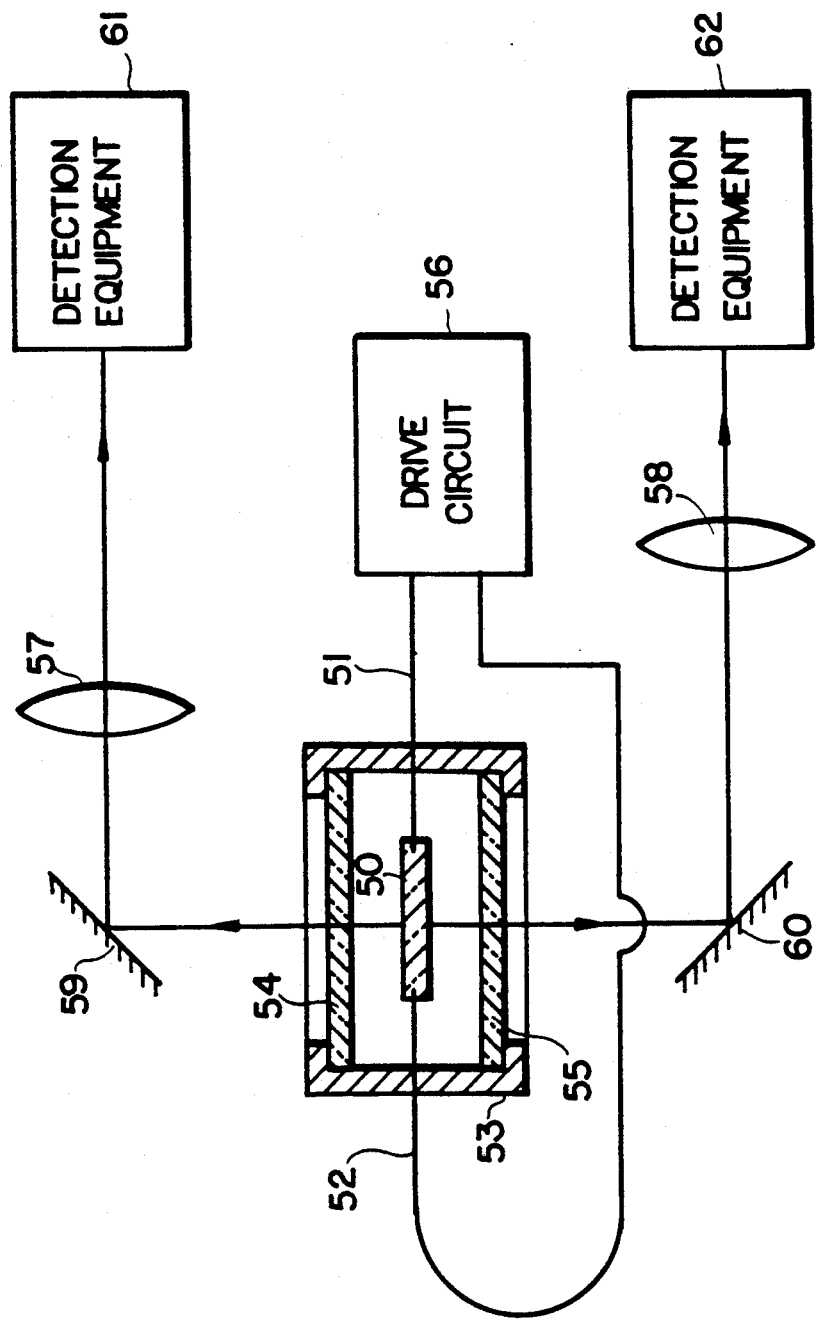

A more detailed presentation of the invention is given below. Reference is made to the drawings, in which all relative measures may be distorted and where FIG. 1 is a schematic perspective view showing a first design of a radiation source with leads for electrical current, FIG. 2 is a schematic perspective view showing a second design of a source consisting of an electrically conducting film deposited onto a nonconductive material, FIG. 3 is an enlarged cut-away portion of a source of the design of FIG. 1 in cross section to show idealized optical relations of importance for its functioning, FIG. 4 is a mostly cross sectional view of a third design of a source contained in a housing with a window for the transmission of thermal radiation, FIG. 5 is a partly cross sectional, partly schematic view of a fourth design of a source between two windows of another housing with an associated drive circuit for the source and detection system for its radiation.

FIG. 1 depicts a source 10 with physical thickness 11 as shown, with electrical supply leads 12 and 13 coupled onto electrical contacts 14 and 15 on the source. To make the source work as intended, its physical thickness must satisfy the conditions formulated in claims 1 or 2. In principle, all sources according to claims 4–7 are shaped as in FIG. 1, being basically plate formed with physical thicknesses very much smaller than their length and width dimensions.

Often the source may be so thin as to be partially transparent to its own radiation. This lowers the effective emissivity. To counteract that, it may be advantageous to make the sources described in claims 4–8 as thick as possible, subject to claims 1 or 2. In practical circumstances, suitable optimum combinations may have to be sought in each separate case.

An interesting eventuality with such thin sources is to have them made from various resistance metals and alloys, for instance combinations of Ni, Cr and Fe, thus retaining sufficient ohmic resistance to heat the sources electrically to elevated temperatures. This possibility is expressed in claim 4. At the same time, such metals and alloys may have high emissivities, above 0.8 for Ni-Cr-Fe and more than 0.9 when oxidized, as specified in claim 5, particularly at high temperatures.

Claim 4 also specifies another relevant source material, metallic glasses, possibly oxidised according to claim 5. These are alloys into which have normally been mixed transition metals and nonmetals, shock cooled from fluid state to preserve the amorphous structure. Metallic glasses are preferentially made into thin foils, with electrical resistances that may vary widely through choice of alloying components. In addition, metallic glasses have good anticorrosion properties. Problems may occur due to recrystallization of the metallic glass when temperatures reach above certain limits. Presently such materials would, therefore, mostly be suitable for sources that operate at relatively low temperatures.

A third relevant alternative is to use semiconductor materials to produce sources according to FIG. 1, as specified in claim 6. These may be made into the desired thicknesses through standard etching techniques. Under normal conditions, several semiconductors may be transparent to infrared radiation, and so are extensively used as optical materials in the infrared. At sufficiently strong doping, however, the semiconductor may acquire so many free charge carriers that it approaches a metal, electrically speaking. Its electric resistance thus may be controlled through doping. Simultaneously the material's absorption of infrared radiation becomes strongly enhanced, resulting in similar increase of its thermal infrared emissivity. The strongest possible doping may often be advantageous, since that multiplies the number of charge carriers, lowers the transparency and increases the source's emissivity to an optimum. Limits for the practically useful doping will be set by the electrical requirements on the drive circuit 56 for the source, cf. FIG. 5 below.

Another alternative embodiment of a source according to FIG. 1 may be to make it from a basically non-conductive material, with one or more electrically conductive materials added as specified in claim 7. Ceramics would constitute particularly relevant starting materials for such sources, in that many ceramics have high melting points and advantageous thermal properties in general, with material structures that allow their composition to be varied within wide limits.

FIG. 2 depicts a source that consists of, chiefly, an electrically non-conductive substrate 20, onto which has been deposited an electrically conductive film 22, with electrical contacts 23 and 24 and supply leads 25 and 26, and whose total physical thickness 21 satisfies claim 1 or 2. In relation to claim 2, it will be the average or effective density and specific thermal capacity of the material combination that enter into the mathematical relation (5) for the thickness of the element. An alternative may be to choose a substrate material that is opaque in the actual spectral region for the source, so that the substrate emits thermal radiation. Possible materials could be, e.g., quartz, alumina and various ceramics, or a thermally resistent glass like Zerodur. Whenever desired, the electrically conductive film may then be made so thin as to not noticeably influence the thermal—and to a limited extent only the optical—properties of the source. Alternatively, a substrate material might be chosen that is transparent to the relevant infrared radiation. The electrically conductive film would then have to serve as emitter, too, and could if necessary be made thicker at the expense of the substrate thickness in order to increase the emissivity. Claim 8 describes both alternatives.

As a result of claims 1 and 2, the sources normally may have thicknesses that are comparable to the wavelengths of the radiation to be generated. In addition, as said above, they may often be partially transparent to the radiation. As in any other electromagnetic structure, this leads to strong interference effects, particularly in directions normal to the element's surface, which is also the main direction of radiation. FIG. 3 thus depicts an idealized cut through a source 30, with physical thickness 31 and optical thickness 32, the optical thickness being a product of the physical thickness with the material's index of refraction. Radiation is also shown as emitted from a point 33 inside the source, with reflections 34 and 35 from the surfaces and transmitted rays 36 and 37. Such reflections result in noticeable interference effects, which may be quite pronounced in materials with large refractive indices, like semiconductors. It may therefore be advantageous to use materials with relatively low indices of refraction, to reduce the surface reflections. Simple antireflection coatings may be introduced, particularly for comparably thick sources and short wavelengths, but only at the expense of the substrate thickness and thus may serve to reduce the effective emissivity.

The interference problem may often be minimized if the optical thickness of the source equals a multiple of half the radiative wavelength, as specified in claim 3. In a solid angle around the normal to the surface, this gives constructive interference which maximizes radiation in the selected spectral interval. Minor thickness variations among sources during production shall not, then, lead to significant changes in the directional and emission characteristics of their thermal radiation at the chosen wavelengths. In order to maintain reproducible conditions, therefore, the interference problem may require sources for different spectral regions to be made with different thicknesses. This also is a new feature in relation to the mentioned existing radiation sources.

FIG. 4 depicts a source 40, with electrical supply leads 41 and 42, mounted within a hermetically sealed container 43 devoid of reactive gases, so that the source may not change its character during operation. As specified in claim 9, it may often be an advantage to mount two or more sources inside the same housing, to change quickly between two or more wavelengths. The housing, which is made from a thermally well-conducting material, encompasses active or passive external cooling means 44 and 45, and has a window 46 that is transparent to infrared radiation. It is a main point about this invention to cool the source between current pulses, thereby to achieve large contrasts in radiation. As long as the source is freely suspended and may radiate without physical obstructions, this presents no problem. The radiation then serves to cool the source, as explained above. With the source mounted inside a container, which may be quite practical, the latter may restrict the radiation leaving the source, and thereby restricts also its cooling. This is a new problem relative to existing sources operated at constant temperatures, in which the housing conducts away most of the supplied energy, and where the temperature of the container may approach that of the source without causing problems for the source's operation.

The source can at no time be colder than its surroundings, which are heated by the source. To make the source reach a low temperature between current pulses, the housing as well as the window must be kept colder than the lowest temperature to be reached by the source when in use, as specified in claim 9. The source shall then have a net heat loss between pulses, too. As far as the housing is concerned, this may be achieved by making its internal walls mirror-like, in addition cooling the housing externally. Radiation from the source shall then mainly be reflected back onto the source or out through the window, while that which becomes absorbed in the walls is conducted away.

As is in addition specified in claim 9, it is also a condition for efficient cooling of the source that the window is transparent across a spectral range that includes the major parts—and preferentially more than 90%—of the total thermal radiation from the source. This, too, is a novel feature compared to existing sources that operate at constant temperatures. For those it is only required that the window be transparent for that particular spectral range which the source delivers. Radiation from the source outside of that spectral region then becomes absorbed in the window to heat it, so that the window may radiate back onto the source to keep it hot. This would make it difficult to cool the present source between current pulses. For the radiation source to work properly, all thermal radiation should be able to leave the source without hindrance. For instance, to transmit 90% of the thermal radiation, the windows must be transparent across a whole decade centered at $\lambda_{max}$, as given by the source's peak temperature according to (2). For a source to work at 3 $\mu$m wavelength, useful windows thus should preferably be transparent in the region 1 to 10 $\mu$m. Sources working at elevated temperatures of 1000K and above, require the windows to be transparent down to, and possibly into, the visible spectral region. Low index window materials may be advantageous, to avoid retroreflections from window surfaces that might reduce the radiative cooling. Broad band anti-reflection coatings centered around $\lambda_{max}$ may also be useful in that context.

FIG. 5 shows one or more sources 50, with electrical supply leads 51 and 52, mounted in a housing 53 with two windows 54 and 55 as specified in claim 10. In other respects the housing and the windows have the same properties as specified in claim 9. Since the source is so thin as to radiate equally well to both sides, this embodiment may be the one that best satisfies the requirements on efficient radiative cooling. The design also makes it possible to utilize the radiation from both sides of the source, as shown in the figure. Schematically shown, too, is an electric drive circuit 56 for the source, as well as lenses 57 and 58 and mirrors 59 and 60 to guide the radiation onto detection equipment 61 and 62. Such equipment is relevant when the source is being applied to infrared spectral analysis, e.g., for the detection of gases. The two sides of the source may then be employed to produce radiation at two different wavelengths, or the radiation from one side may be used as a reference against which to identify minor changes in radiation from the other side when traversing a volume of gas. In both cases, as in several different examples that may easily be imagined, a source with two windows offers obvious constructive benefits, while economizing on radiation since beam splitters may not be required.

The present invention thus enables one to produce pulses of infrared radiation, with practically constant intensity, up to the frequency f that enters into relation (5). The source may thereby be electronically controlled like any other circuit element. It may then also be possible, e.g., to pulse code the radiation from such an element. This will make the source useful in termal printers, while such coding may also be exploited in more advanced spectroscopic connections. Moreover, for a given radiative intensity, the source requires significantly less energy supplied than do similar known sources. Further and substantial constructive simplifications, in spectroscopic and analytic equipment, may be realized by utilizing the radiation from both sides of the source.

What is claimed is:

1. Infrared radiation source comprising a thin, plate shaped and at least partly electrically conductive element, and energizing means for energizing the electrically conductive part of the element with pulsating electric current, whereby to vary the temperature of the element between a highest and lowest value, a physical thickness of the element being so small that thermal energy stored in the element during one pulse of the electric current is less than thermal energy radiated from the element in the course of the same pulse of the electric current.

2. Infrared radiation source according to claim 1, wherein the element's physical thickness t satisfies the relation $$t < 8\epsilon\sigma T^3/C\rho f, \quad (5)$$

where the sign "<", means "less than", $C$ [J/g·K] is the specific thermal capacity, $\rho$ [g/cm$^3$] the effective density and $\epsilon < 1$ the emissivity of the material/combination of materials in the element, $\sigma = 5.67 \cdot 10^{-12}$ [W/cm$^2$K$^4$] is the Stefan-Boltzmann constant, $T$ [K] is the temperature to which the element becomes heated during each pulse of electric current and $f$ [Hz] is the frequency of the current pulses.

3. Infrared radiation source according to claim 2, wherein the optical thickness of the element, $l = n \cdot t$, where n is the index of refraction of the element material and t its physical thickness, as far as possible corresponds to a multiple of half the center wavelength of the desired thermal radiation from the element.

4. Infrared radiation source according to claim 1, wherein the element has been made from a semiconductor material.

5. Infrared radiation source according to claim 4, wherein the semiconductor material is doped.

6. Infrared radiation source according to claim 4, wherein the element is hermetically encapsulated in a housing devoid of reactive gases and with at least one infrared-transmitting window on at least one of opposite sides of the housing, external walls of the housing having cooling means for maintaining the temperature of the housing below the lowest value of the temperature of the element, a range of spectral transmission of the window being so wide that it encompasses a major part of the thermal energy radiated from the element.

7. Infrared radiation source according to claim 1, wherein the element has been made from a basically non-conductive material into which has been mixed at least one electrically conductive substance.

8. Infrared radiation source according to claim 7, wherein the element is hermetically encapsulated in a housing devoid of reactive gases and with at least one infrared-transmitting window on at least one of opposite sides of the housing, external walls of the housing having cooling means for maintaining the temperature of the housing below the lowest value of the temperature of the element, a range of spectral transmission of the window being so wide that it encompasses a major part of the thermal energy radiated from the element.

9. Infrared radiation source according to claim 1, wherein the element has been made from a basically non-conductive material onto which has been deposited an electrically conductive film.

10. Infrared radiation source according to claim 9, wherein the element is hermetically encapsulated in a housing devoid of reactive gases and with at least one infrared-transmitting window on at least one of opposite sides of the housing, external walls of the housing having cooling means for maintaining the temperature of the housing below the lowest value of the temperature of the element, a range of spectral transmission of the window being so wide that it encompasses a major part of the thermal energy radiated from the element.

11. Infrared radiation source according to claim 3, wherein the element is hermetically encapsulated in a housing devoid of reactive gases and with at least one infrared-transmitting window on at least one of opposite sides of the housing, external walls of the housing having cooling means for maintaining the temperature of the housing below the lowest value of the temperature of the element, a range of spectral transmission of the window being so wide that it encompasses a major part of the thermal energy radiated from the element.

12. Infrared radiation source according to claim 2, wherein the element is hermetically encapsulated in a housing devoid of reactive gases and with at least one infrared-transmitting window on at least one of opposite sides of the housing, external walls of the housing having cooling means for maintaining the temperature of the housing below the lowest value of the temperature of the element, a range of spectral transmission of the window being so wide that it encompasses a major part of the thermal energy radiated from the element.

13. Infrared radiation source according to claim 2, wherein the element material consists of a metal or a metal alloy comprising Ni, Cr, Fe and/or metallic glasses.

14. Infrared radiation source according to claim 13, wherein surfaces of the element have been oxidized.

15. Infrared radiation source according to claim 14, wherein the element is hermetically encapsulated in a housing devoid of reactive gases and with at least one infrared-transmitting window on at least one of opposite sides of the housing, external walls of the housing having cooling means for maintaining the temperature of the housing below the lowest value of the temperature of the element, a range of spectral transmission of the window being so wide that it encompasses a major part of the thermal energy radiated from the element.

16. Infrared radiation source according to claim 13, wherein the element is hermetically encapsulated in a housing devoid of reactive gases and with at least one infrared-transmitting window on at least one of opposite sides of the housing, external walls of the housing having cooling means for maintaining the temperature of the housing below the lowest value of the temperature of the element, a range of spectral transmission of the window being so wide that it encompasses a major part of the thermal energy radiated from the element.

17. Infrared radiation source according to claim 1, wherein the element is hermetically encapsulated in a housing devoid of reactive gases and with an infrared-transmitting window on one side of the housing, external walls of the housing having cooling means for maintaining the temperature of the housing below the lowest value of the temperature of the element, a range of spectral transmission of the window being so wide that it encompasses a major part of the thermal energy radiated from the element.

18. Infrared radiation source according to claim 17, characterized in that a similar infrared-transmitting window is on the other side (the rear side) of the element respectively the elements.

19. Infrared radiation source according to claim 17, wherein the major part of the total thermal radiation is more than 90% thereof.

20. Infrared radiation source according to claim 1, wherein the optical thickness of the element, $l = n \cdot t$, where n is the index of refraction of the element material and t its physical thickness, as far as possible corresponds to a multiple of half the center wavelength of the desired thermal radiation from the element.

21. Infrared radiation source according to claim 1, wherein the element material consists of metal or a metal alloy comprising Ni, Cr, Fe. and/or metallic glasses.

22. Infrared radiation source according to claim 21, wherein surfaces of the element have been oxidized.

23. Infrared radiation source according to claim 20, wherein the element has been made from a semiconductor material.

24. Infrared radiation source according to claim 20, wherein the element has been made from a basically non-conductive material into which has been mixed at least one electrically conductive substance.

25. Infrared radiation source according to claim 20, wherein the element has been made from a basically non-conductive material onto which has been deposited an electrically conductive film.

* * * * *